US008093667B2

(12) United States Patent
Doron et al.

(10) Patent No.: US 8,093,667 B2
(45) Date of Patent: Jan. 10, 2012

(54) FLEXIBLE GATE ELECTRODE DEVICE FOR BIO-SENSING

(75) Inventors: Amihood Doron, Ahuzat Barak (IL); Ilan Levy, Harif (IL)

(73) Assignee: Intel Corporation, Santa Clara, CA (US)

( * ) Notice: Subject to any disclaimer, the term of this patent is extended or adjusted under 35 U.S.C. 154(b) by 763 days.

(21) Appl. No.: 12/165,200

(22) Filed: Jun. 30, 2008

(65) Prior Publication Data

US 2009/0321276 A1    Dec. 31, 2009

(51) Int. Cl.
*G01N 27/26* (2006.01)
(52) U.S. Cl. .................. 257/415; 204/403.01; 205/777.5
(58) Field of Classification Search ................... 257/415
See application file for complete search history.

(56) References Cited

U.S. PATENT DOCUMENTS

| | | | |
|---|---|---|---|
| 5,852,229 A * | 12/1998 | Josse et al. ................... | 73/24.06 |
| 6,325,904 B1 * | 12/2001 | Peeters .......................... | 257/414 |
| 7,129,554 B2 * | 10/2006 | Lieber et al. ................... | 257/414 |
| 7,291,466 B2 * | 11/2007 | Su et al. ............................. | 435/6 |
| 7,291,496 B2 * | 11/2007 | Holm-Kennedy ......... | 435/287.2 |
| 7,439,666 B1 * | 10/2008 | Liu et al. ....................... | 313/495 |
| 7,910,064 B2 * | 3/2011 | Hamilton et al. .......... | 422/82.01 |
| 2003/0215816 A1 * | 11/2003 | Sundararajan et al. ............ | 435/6 |
| 2003/0215863 A1 * | 11/2003 | Chow et al. ......................... | 435/6 |
| 2005/0262943 A1 * | 12/2005 | Claydon et al. ................. | 73/579 |
| 2006/0021881 A1 * | 2/2006 | Soundarrajan et al. .... | 205/777.5 |
| 2007/0145966 A1 * | 6/2007 | Shekhawat et al. .......... | 324/71.1 |
| 2007/0215465 A1 * | 9/2007 | Gu ........................... | 204/403.01 |

OTHER PUBLICATIONS

Machauf, Andrew et al., "Hydrogel-Based MEMS Biosensor", U.S. Patent Application Filed Dec. 26, 2007 assigned U.S. Appl. No. 11/964,179.
Sidorenko, Alexander et al., "Reversible Switching of hydrogel-Actuated Nanostructures into Complex Micropaterns", Science, vol. 315, 487; DOI: 10.1126/science.1135516, (Jan. 26, 2007), 5 pgs.
Shekhawat, Gajendra et al., "MOSFET—Embedded Microcantilevers for Measuring Deflection in Biomolecular Science", Science vol. 311, (Mar. 17, 2006), pp. 1592-1595.
Miyata, Takashi et al., "A reversibly antigen-responsive hydrogel", Nature, vol. 399; 1999 Macmillan Magazines Ltd., (Jun. 24, 1999), pp. 766-769.
Liu, Robin H., et al., "Fabrication and Characterization of Hydrogel-Based Microvalves", IEEE Journal of Microelectromechanical Systems vol. 11, No. 1, (Feb. 2002), pp. 45-53.
Hilt, J. Z., et al., "Ultrasensitive Biomems Sensors Based on Microcantilevers Patterned with Environmentally Responsive Hydrogels", Biomedical Microdevices 5:3, (2003), pp. 177-184.
Jaeger, Richard C., et al., "CMOS Stress sensors on (100) Silicon", IEEE Journal of Solid State Circuits, vol. 35, No. 1, (Jan. 2000), pp. 85-95.
Li, Z. et al., "Sequence-Specific Label-Free DNA Sensors Based on Silicon Nanowires", Nano Letters 2004, vol. 4, No. 2, (2004), pp. 245-247.

(Continued)

*Primary Examiner* — N Drew Richards
*Assistant Examiner* — Robert Carpenter
(74) *Attorney, Agent, or Firm* — Cool Patent, P.C.; Joseph P. Curtain

(57) ABSTRACT

Briefly, disclosed is an apparatus and method for detecting an analyte wherein a flexible gate electrode may respond to mechanical stress and/or electrostatic changes induced by bonding of a biomolecular probe and an analyte.

14 Claims, 2 Drawing Sheets

OTHER PUBLICATIONS

Cahen, David et al., "The Cooperative Molecular Field Effect", Advanced Functional Materials, 2005, 15, (2005), pp. 1571-1578.

Balasubramanian, Anupama et al., "Si-Based Sensor for Virus Detection", IEEE Sensors Journal, vol. 5, No. 3, (Jun. 2005), pp. 340-344.

Goldberger, Josh et al., "Silicon Vertically Integrated Nanowire Field Effect Transistors", Nano Letters 2006, vol. 6, No. 5; American Chemical Society, (2006), pp. 973-977.

Schmidt, Volker et al., "Realization of a Silicon Nanowire Vertical Surround-Gate Field-Effect", Small 2006, 2, No. 1, (2006), pp. 85-88.

Bashir, R. et al., "Micromechanical cantilever as an ultrasensitive pH microsensor", Applied Physics letters vol. 81, Num. 16, (Oct. 14, 2002),pp. 3091-3093.

Machauf, Andrew, et al., "Hydrogel Chemical Sensor", U.S. Appl. No. 11/967,140, filed Dec. 29, 2007.

A. Poghossian, et al., "Field-effect sensors for monitoring the layer-by-layer adsorption of charged macromolecules", ScienceDirect Sensors and Actuators B 18, 2006, pp. 163-170.

Kamahori, Masao, et al., "A novel enzyme immunoassay based on potentiometric measurement of molecular adsorption events by an extended-gate field-effect transistor sensor", ScienceDirect Biosensors and Bioelectronics 22, 2007, pp. 3080-3085.

\* cited by examiner

FLEXIBLE GATE ELECTRODE DEVICE FOR BIO-SENSING

BACKGROUND

Technical Field

The disclosure relates to chemical sensors, more particularly the disclosure relates to a solid-state sensor capable of chemical sensing and including an integrated cantilever, rod, cylinder and/or plane.

DETAILED DESCRIPTION

In the following detailed description, numerous specific details are set forth in order to provide a thorough understanding of claimed subject matter. It will be, however, understood by those skilled in the art that claimed subject matter may be practiced without these specific details. In other instances, well-known methods, procedures, and components have not been described in detail so as not to obscure claimed subject matter.

Throughout the following disclosure the term 'biosensor' is used and is intended to refer to a device capable of detection of an analyte that combines a biological component with an electronic or mechanical detector element. The terms 'biomolecule' and 'biomolecular' are used throughout the following disclosure and are intended to refer to one or more molecules that may be biologically active and may be naturally occurring in living organisms or may be synthesized via a variety of non-naturally occurring pathways. The term 'analyte' is used throughout the following disclosure and is intended to refer to any chemical or biological constituent that is undergoing analysis. The term 'probe' is used throughout the following disclosure and is intended to refer to any identifiable substance that may be used to detect, isolate, or identify another substance. A probe may be capable of covalent and non-covalent bonding to a specific analyte and/or may be capable of undergoing a molecular recognition event with an analyte. During a molecular recognition event an interaction between a probe and an analyte may occur giving rise to specific or selective recognition of an analyte. A probe may bind selectively and/or specifically to an analyte. Specific binding is the specific recognition of a particular chemical, molecule and/or cell compared to substantially less recognition of other chemicals, molecules and/or cells.

Throughout the following disclosure particular embodiments of a solid-state chemical sensor are disclosed. Biomolecular sensors for detecting analytes comprising various species of biomolecules are discussed. The device and method disclosed herein may, however, be useful for detecting many varieties of organic and inorganic chemicals and compounds using organic and inorganic chemicals and compounds as probes and claimed subject matter is not limited in this regard.

Further, throughout the following disclosure field effect transistors comprising flexible-gate electrodes are disclosed. Such field effect transistors may comprise any of a variety of field effect transistors, such as a FinFET, trigate FET and/or four gate FET and claimed subject matter is not limited in this regard.

Figure 1:
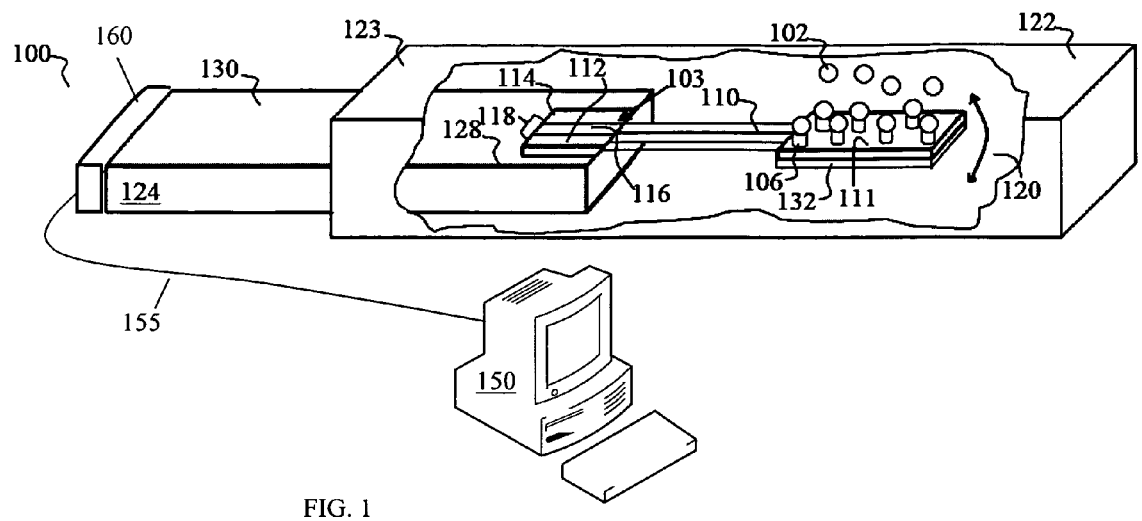
FIG. 1 is a diagram of a particular embodiment of a biosensor for detecting the presence of an analyte in a sample.

FIG. 1 illustrates a biosensor 100 capable of detecting an analyte 102 from sample 122. In a particular embodiment, the sample may be in solid, liquid and/or gas phase. In a particular embodiment, biosensor 100 may comprise an embedded field effect transistor (FET) 103 disposed on substrate 124. FET 103 may comprise channel 118 extending between source 112, and drain 114 via gate 116. FET 103 may further comprise flexible-gate electrode (FGE) 110. In a particular embodiment, source 112, gate 116 and drain 114 may be disposed within substrate 124. FGE 1 10 may be coupled to source 112 and drain 114 and extend therefrom into sample 122. According to a particular embodiment, one or more biomolecular probes 106 may be disposed on an outside surface of FGE 110. In a particular embodiment, detection may be measured by a signal induced by FET 103 in response to recognition of analyte 102.

In a particular embodiment, substrate 124 may be comprised of a variety of materials, such as, for instance: silicon, silicon-oxide, gallium arsenide, silicon germanium, silicon carbide, gallium phosphide and/or polysilicon and claimed subject matter is not so limited. According to a particular embodiment, an outside surface 128 of substrate 124/FET 103 assembly may be sealed with coating 130 that may be substantially impermeable to a variety of substances in a variety of physical phases and claimed subject matter is not so limited. Coating 130 may comprise any of a variety of materials, such as, polyimde, wax and/or gum and claimed subject matter is not limited in this regard. Such coating 130 may enable biosensor 100 to be immersed in a liquid or gas sample, be used repeatedly while resisting wear and reduce device failure. This is, however, merely an example of a method of protecting an outside surface 128 of substrate 124/FET 103 assembly and claimed subject matter is not so limited.

In a particular embodiment, FGE 110 may function as FET 103 gate electrode and may be coupled to and extend from gate 116. FGE 1 10 may comprise charge-sensitive materials such as, for instance, monolayers of siloxan comprising protons and metal ion sensitive head groups (for example, amine, carboxyl, pyridine, nitrilotriacetate (NTA), thiophen, pyrol etc.) and claimed subject matter is not limited in this regard. According to a particular embodiment, FGE 110 may have a high aspect ratio and may comprise a variety of structures, such as, for instance a: cantilever, blade, cylinder and/or nanowire and claimed subject matter is not limited in this regard.

In a particular embodiment, FGE 110 may be directly in contact with the ambient, such as, sample 122. In another particular embodiment, FGE 110 may comprise a selectively permeable or reactive coating, such as, for instance, a lipid bilayer, hydrogel, polyvinyl acetate (PVA) and polyethylene glycol (PEG) based functional polymers and/or polyelectrolyte and claimed subject matter is not limited in this regard. In a particular embodiment, FGE 110 may have a paddle shape and probes 106 may be located on a distal end of FGE 110 with respect to FET 103. This is, however, merely an example of a shape and an assembly of an FGE and claimed subject matter is not limited in this regard. For example, FGE may have a blade shape and probes may be distributed evenly about a surface of the blade.

According to a particular embodiment, biosensor 100 may comprise support structure 132 coupled to FGE 110 and may be capable of providing FGE 110 with additional support. Support structure 132 may have a high aspect ratio and may comprise a variety of structures, such as, for instance a: cantilever, blade, cylinder and/or nanowire and claimed subject matter is not limited in this regard. In a particular embodiment, support structure 132 may comprise a variety of materials such as, for instance; quartz crystal, ceramic, silicon, silicon-oxide, gallium arsenide, silicon germanium, silicon carbide, gallium phosphide and/or polysilicon and claimed subject matter is not limited in this regard. This is, however, merely an example of an assembly of a biosensor comprising an FGE and support structure and claimed subject matter is not limited in this regard. For instance, in another particular embodiment, an FGE may extend from a FET without additional supporting structures (See FIG. 2).

In conventional solid-state sensor detection methods, often electrical drift and a low signal-to-noise (SIN) ratio have a negative impact on accuracy. Here, FGE 110 may exert both mechanical stress on FET 103 and change channel mobility in gate 116. This may enable greater sensitivity than conventional methods, as biosensor 100 may be set to sense multiple forces acting on FGE 110 in response to a bio-molecular recognition event.

According to a particular embodiment, upon detection of biomolecular analyte 102, FGE 110 may exert both mechanical stress on FET 103 and induce an electrostatic charge in gate 116. A bio-molecular specific recognition event between probes 106 and analyte 102 may deflect FGE 110, along an arc 120. Such deflection may be due to steric and/or electrostatic forces brought on by binding of probes 106 with biomolecular analytes 102. Deflection of FGE 110 may induce strain on FET 103 which may transform into conductivity effects in channel 118. For example, such strain, may stress channel 118 under FGE 110 enabling mobility modulation of charge carriers in channel 118. According to another particular embodiment, deflection of FGE 110 may result in reduced charge-carrier mobility (in other words, a decrease in current). Mechanical stress may induce additional scattering centers in substrate 124 changing the mobility of charge carriers.

Additionally, in a particular embodiment, charge-density rearrangement of analyte 102 may occur during such a recognition event. Such charge-density rearrangement may change the net charge of analyte 102 and enable a surface potential on FGE 110. Such a change in the surface potential in FGE 110 may modulate channel conductivity by changing a voltage on gate 116.

In a particular embodiment, mechanical and electrostatic effects of a specific recognition event on FGE 110 may be synergized. According to a particular embodiment, synergizing the mechanical and electrostatic effects of a recognition event may amplify biosensor 100's sensitivity to analyte 102. For instance, in a particular embodiment, in which a deflection of the FGE 110 results in reduced charge carrier mobility in channel 118, FGE 110 may be prepared such that a surface potential resulting from analyte 102-probe 106 interaction may be lower than an initial potential. Such a synergy between mechanical and electrostatic effects may be obtained by interaction of analyte 102 with a charged head group on FGE 110 that may screen the charge of a monolayer on FGE 110. For example, where FET 103 is an n-channel device, a monolayer charged head group on FGE 110 may be positively charged and analyte 102 may be negatively charged. In another particular embodiment, FET 103 may be a p-channel device, a monolayer charged head group on FGE 110 may be negatively charged and analyte 102 may be positively charged. These are, however, merely examples of method of synergizing mechanical and electrostatic effects of analyte/probe interaction in a FET comprising a FGE and claimed subject matter is not limited in this regard.

In a particular embodiment, biosensor 100 may be fabricated in a variety of dimensions, such as, microscale or nanoscale fabrication and claimed subject matter is not limited in this regard. For instance, in a particular embodiment, FGE 110 may be 1000 nm×5000 nm×10000 nm and substrate 124 may be 500 pm×2000 pm×2000 pm. This is, however, merely an example of biosensor 100 dimensions and claimed subject matter is not limited in this regard.

In a particular embodiment, probe 106 coupled to outside surface 111 of FGE 110 may be capable of forming a bond to analyte 102 and thereby inducing electrostatic effects and mechanical stress on FGE 110 due to steric and/or electrochemical effects of bonding. In another particular embodiment, FGE 110 may be coupled to a variety of probes that may be capable of bonding to different analytes. Thus, a biosensor as disclosed herein may be capable of detecting and bonding to one or more analytes to enable detection of different analytes in the same sample. These are, however, merely examples of probe configurations for a biosensor and claimed subject matter is not so limited.

In a particular embodiment, probe 106 may comprise a variety of biomolecular species, such as: antibodies, antibody fragments, single-chain antibodies, genetically engineered antibodies, oligonucleotides, polynucleotides, nucleic acids, nucleic acid analogues, peptide nucleic acids, proteins, peptides, binding proteins, receptor proteins, transport proteins, lectins, substrates, inhibitors, activators, ligands, hormones, neurotranamitters, growth factors, cytokines, carbohydrates, aptamers, lipids, lipid bilayers and/or charged polymers and claimed subject matter is not limited in this regard.

In a particular embodiment, analytes 102 may comprise a variety of biomolecular species, such as: amino acid, peptide, polypeptide, protein, glycoprotein, lipoprotein, antibody, nucleoside, nucleotide, oligonucleotide, nucleic acid, sugar, carbohydrate, oligosaccharide, polysaccharide, fatty acid, lipid, hormone, metabolite, growth factor, cytokine, chemokine, receptor, neurotransmitter, antigen, allergen, antibody, substrate, metabolite, cofactor, inhibitor, drug, pharmaceutical, nutrient, biohazardous agent, infectious agent, prion, vitamin, heterocyclic aromatic compound, carcinogen, mutagen, waste product, virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen, prion and/or a cell and claimed subject matter is not limited in this regard.

In a particular embodiment, biosensor 100 may be exposed to sample 122 by a variety of methods, such as, for instance, by titrating an aqueous sample 122 containing analyte 102 directly onto a particular portion of FGE 110 or by exposing a portion of FGE 110 to a gas carrier containing analyte 102 and claimed subject matter is not limited in this regard. In a particular embodiment, biosensor 100 may be partially enclosed in package 123. Package 123 may be configured in a variety of ways and claimed subject matter is not limited in this regard. In a particular embodiment, FET 103 may send a signal to a detecting unit 160 which may communicate detection of an analyte to a processing unit 150, such as a computer CPU and/or mobile unit processor and claimed subject matter is not limited in this regard. In another particular embodiment, FET 103 may communicate directly with processing unit 150 and claimed subject matter is not limited in this regard. Communication may be via communication line 155 by any of a variety of communication techniques, such as for instance via wireline and/or wireless communication and claimed subject matter is not limited in this regard.

Figure 2:
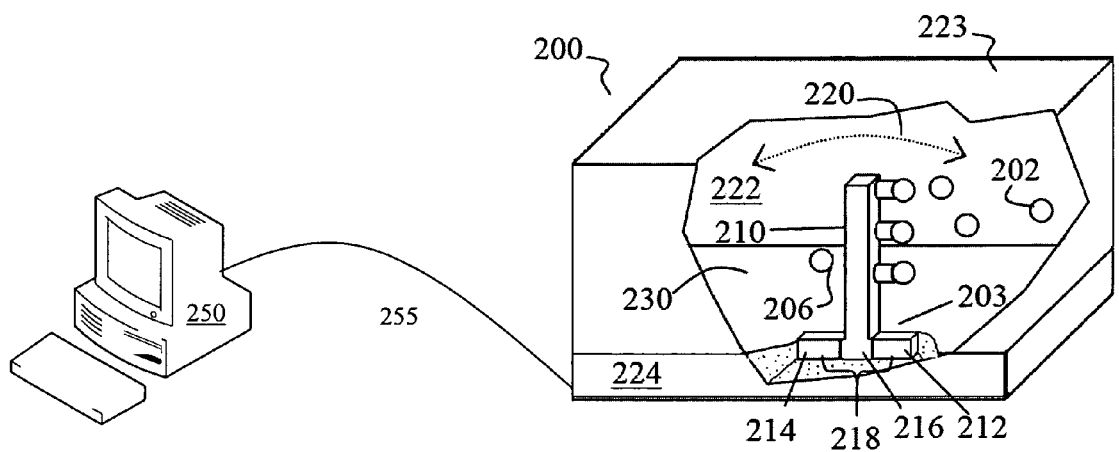
FIG. 2 is a diagram of a particular embodiment of a biosensor for detecting the presence of an analyte in a sample.

FIG. 2 illustrates a particular embodiment of a biosensor 200 for detecting analyte 202. In a particular embodiment, biosensor 200 may be immersed in sample 222 within package 223. In a particular embodiment, biosensor 200 may comprise FET 203 embedded in substrate 224. According to a particular embodiment, an outside surface of substrate 2241FET 203 assembly may be sealed with impermeable coating 230. This is, however, merely an example of a method of protecting an outside surface of substrate 224/FET 203 assembly and claimed subject matter is not so limited.

In a particular embodiment, FGE 210 may function as FET 203 gate electrode and may be coupled to and extend from gate 216. As noted above, FGE 210 may comprise charge-sensitive material such as, for instance, monolayers of siloxan comprising protons and metal ion sensitive head groups (for example, amine, carboxyl, pyridine, nitrilotriacetate (NTA), thiophen, pyrol etc.) and claimed subject matter is not limited in this regard. In a particular embodiment, FGE 210 may be directly in contact with the ambient, such as, sample 222. In a particular embodiment, FGE 210 may have a substantially rectangular shape. FGE 210 may comprise or be in contact with an analyte-senstive material such as a biomolecular probe and/or hydrogel and claimed subject matter is not limited in this regard. According to a particular embodiment, probes 206 may be located on a single side of FGE 206 to enable mechanical stress to flex FGE 210 along arc 220. This is, however, merely an example of a shape of an FGE and placement of probes and claimed subject matter is not so limited.

According to a particular embodiment, upon detection of biomolecular analyte 202, FGE 210 may exert both mechanical stress on FET 203 and induce an electrostatic charge in gate 216. A bio-molecular specific recognition event between probes 206 and analyte 202 may deflect FGE 210, along an arc 220 and may induce strain on FET 203 which may transform into conductivity effects in channel 218. Additionally, charge density rearrangement of analyte 202 may change a surface potential change on FGE 210 changing gate 216 voltages.

In a particular embodiment, biosensor 200 may be immersed in sample 222 contained in package 223. Package 223 may be configured in a variety of ways and claimed subject matter is not limited in this regard. In a particular embodiment, biosensor 200 may communicate detection of an analyte to a processing unit 250, such as a computer CPU and/or mobile unit processor and claimed subject matter is not limited in this regard. Communication may be via communication line 255 by any of a variety of communication techniques, such as for instance via wireline and/or wireless communication and claimed subject matter is not limited in this regard.

In another particular embodiment, biosensor 200 may comprise a sensitive hydrogel (not shown). Such a hydrogel may be sensitive to a variety of stimuli and substances. Upon recognition of a substance or stimulus to which a hydrogel is sensitive, the volume of the hydrogel may change. According to a particular embodiment, FGE 210 may be in contact with a hydrogel and such a change in volume may deflect FGE 210, along an arc 220 and may induce strain on FET 203 which may transform into conductivity effects in channel 218. Additionally, charge density rearrangement of analyte 202 may change a surface potential change on FGE 210 changing gate 216 voltages. In a particular embodiment, such a hydrogel may be immobilized on a surface of FGE 210 and/or FGE 210 may be immersed in a sensitive hydrogel within an enclosed package. According to a particular embodiment, a sensitive hydrogel may comprise one or more biomolecular probes sensitive to one or more analytes. These are, however, merely examples of a biosensor 200 comprising a hydrogel and claimed subject matter is not limited in this regard.

Figure 3:
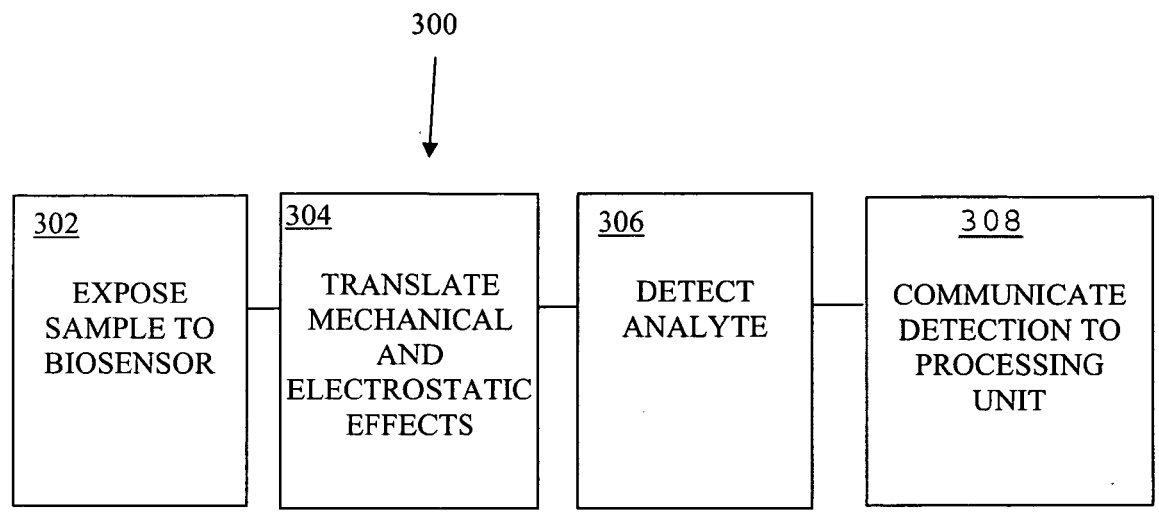
FIG. 3 is a block diagram illustrating a particular embodiment of a process for detecting the presence of an analyte in a sample.

FIG. 3 is a block diagram illustrating a method 300 for detecting an analyte. At block 302, an analyte sample may be put in contact with a biosensor comprising a field effect transistor, one or more biomolecular probes and a flexible-gate electrode. In another particular embodiment, biosensor 300 may comprise an array of FETs (see, for example FIG. 4) comprising flexible-gate electrodes having one or more biomolecular probes disposed thereon and claimed subject matter is not limited in this regard. In a particular embodiment, a flexible-gate electrode may be sensitive to electrostatic and mechanical effects of bonding between an analyte and probe. According to a particular embodiment, a FGE may be constructed to synergize electrostatic and mechanical effect of bonding to enable enhanced detection of an analyte as described above with respect to FIG. 1. At block 304, upon exposure to a sample, electrostatic and mechanical effects of bonding between a probe and analyte may translate via a flexible-gate electrode into a signal in a field effect transistor. At block 306, a biosensor may detect the presence of an analyte in the sample based at least in part on detection of electrostatic and mechanical effects translated via flexible-gate electrode. At block 308, detection of an analyte may be registered by an information processing system such as an on-chip electronic circuit for processing and/or a computer. This is, however, merely an example of a process for detecting an analyte using a biosensor comprising a flexible-gate electrode and claimed subject matter is not limited in this regard.

Figure 4:
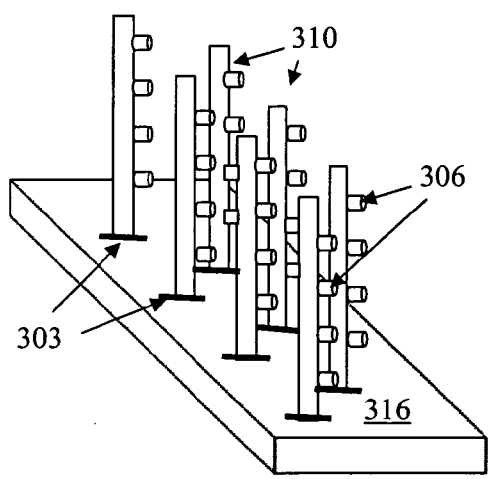
FIG. 4 is a diagram illustrating a particular embodiment of a biosensor comprising a multiple flexible-gate electrode array.

FIG. 4 illustrates a particular embodiment of biosensor 300 comprising a multiple FGE 310 array. In a particular embodiment, biosensor 300 may comprise a plurality of embedded FETs 303 comprising FGEs 310 arranged on a surface of substrate 316. In a particular embodiment, FGEs 303 may comprise biomolecular probes 306 capable of bonding to an analyte (not shown) in a sample. According to another particular embodiment, one or more FETs 303 of FGE array 310 may comprise biomolecular probes 306 sensitive to one or more different types of analytes and claimed subject matter is not limited in this regard. This is, however, merely an example of an arrangement of a biosensor comprising a multiple FET array and claimed subject mater is not limited in this regard.

While certain features of claimed subject matter have been illustrated as described herein, many modifications, substitutions, changes and equivalents will now occur to those skilled in the art. It is, therefore, to be understood that the appended claims are intended to cover all such embodiments and changes as fall within the spirit of claimed subject matter.

What is claimed is:

1. An apparatus for detecting an analyte, comprising:
a substrate;
a first field effect transistor (FET), the first FET comprising a source, a drain, a gate and a channel, the first FET being coupled to the substrate, and a carrier mobility of the channel changing in response to a mechanical stress exerted on the channel;
a first flexible-gate electrode mechanically coupled to the gate, the first flexible-gate electrode
extending from the substrate, and
being operable to flex in response to mechanical stress and exert a mechanical stress on the channel of the first FET; and an analyte-sensitive material coupled to an outside surface of the first flexible-gate electrode, the analyte sensitive material being operable to react to an analyte and generate a mechanical stress that flexes the first flexible-gate electrode and induces a mechanical stress on the channel of the first FET that changes the carrier mobility of the channel.

2. The apparatus of claim 1, wherein the analyte-sensitive material comprises one or more biomolecular probes.

3. The apparatus of claim 1, wherein the analyte-sensitive material comprises a hydrogel.

4. The apparatus of claim 1, further comprising;
a detecting unit coupled to the first FET and operable to process a signal from the first FET to detect the presence of an analyte; and
a processing unit communicatively coupled to the detecting unit, the processing unit being operable to receive communication from the detecting unit.

5. The apparatus of claim 1, wherein the first flexible-gate electrode comprises a charge sensitive material.

6. The apparatus of claim 3, wherein the first flexible-gate electrode further comprises; a monolayer of siloxan comprising protons or metal ion sensitive head groups comprising amine, carboxyl, pyridine, nitrilotriacetate (NTA), thiophen or pyrol, or combinations thereof.

7. The apparatus of claim 1, further comprising a support member coupled to the first flexible-gate electrode.

8. The apparatus of claim 1, wherein the first flexible-gate electrode comprises a coating, and wherein the coating is selectively permeable or charged, or combinations thereof.

9. The apparatus of claim 1, wherein the first flexible-gate electrode comprises a coating comprising a lipid bilayer, hydrogel, polyvinyl acetate (PVA), a polyethylene glycol (PEG) based functional polymer or polyelectrolyte, or combinations thereof.

10. The apparatus of claim 1, wherein the substrate comprises a coating disposed on an outside surface of the substrate, and wherein the coating is substantially impermeable to liquids or gases, or combinations thereof.

11. The apparatus of claim 2, wherein the one or more biomolecular probes comprise: antibodies, antibody fragments, single-chain antibodies, genetically engineered antibodies, oligonucleotides, polynucleotides, nucleic acids, nucleic acid analogues, peptide nucleic acids, proteins, peptides, binding proteins, receptor proteins, transport proteins, lectins, substrates, inhibitors, activators, ligands, hormones, neurotranamitters, growth factors, cytokines, carbohydrates, aptamers, lipids, lipid bilayers or charged polymers, or combinations thereof.

12. The apparatus of claim 1, wherein the analyte comprises a(n): acid, base, organic compound, inorganic chemical, amino acid, peptide, polypeptide, protein, glycoprotein, lipoprotein, antibody, nucleoside, nucleotide, oligonucleotide, nucleic acid, sugar, carbohydrate, oligosaccharide, polysaccharide, fatty acid, lipid, hormone, metabolite, growth factor, cytokine, chemokine, receptor, neurotransmitter, antigen, allergen, antibody, substrate, metabolite, cofactor, inhibitor, drug, pharmaceutical, nutrient, biohazardous agent, infectious agent, prion, vitamin, heterocyclic aromatic compound, carcinogen, mutagen, waste product, virus, bacterium, *Salmonella, Streptococcus, Legionella, E. coli, Giardia, Cryptosporidium, Rickettsia*, spore, mold, yeast, algae, amoebae, dinoflagellate, unicellular organism, pathogen, prion or a cell, or combinations thereof.

13. The apparatus of claim 1, further comprising a package capable of containing a sample comprising the analyte in an inside portion of the package, and wherein the first flexible-gate electrode is disposed within the inside portion of the package.

14. The apparatus of claim 2, further comprising a plurality of FETs disposed on the substrate, one or more of the plurality of FETs comprising a source, a drain, a gate and a channel and being coupled to the substrate, a carrier mobility of the channel changing in response to a mechanical stress exerted on the channel, one or more of the plurality of FETs comprise flexible-gate electrodes comprising one or more biomolecular probes, the plurality of flexible-gate electrodes
extending from the substrate, and
being operable to flex in response to mechanical stress and exert a mechanical stress on the channels of first FET; and
wherein the one or more biomolecular probes are sensitive to one or more analytes.

* * * * *